Figure 1:
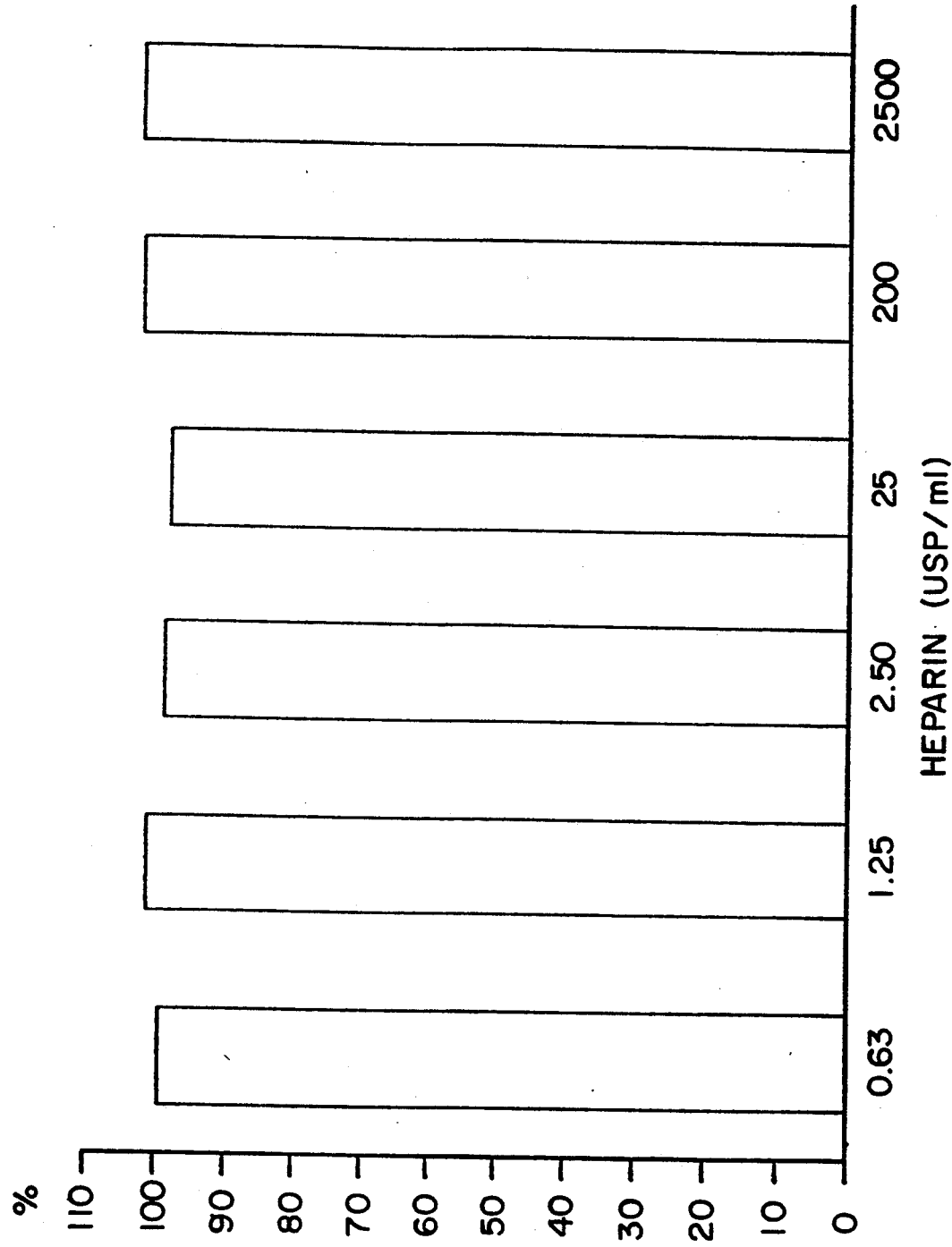

United States Patent [19]

Sawyer et al.

[11] Patent Number: 5,279,824
[45] Date of Patent: Jan. 18, 1994

[54] PHARMACEUTICAL FORMULATION CONTAINING HEPARIN AND ENDO-BETA-GLUCURONIDASE, USEFUL FOR THE TREATMENT OF THROMBOSIS

[75] Inventors: Roy T. Sawyer; Christopher Powell-Jones, both of Llandeilo, United Kingdom

[73] Assignee: Merck Patent GmbH, Darmstadt, Fed. Rep. of Germany

[21] Appl. No.: 973,565

[22] Filed: Nov. 9, 1992

Related U.S. Application Data

[63] Continuation of Ser. No. 840,617, Feb. 20, 1992, abandoned, which is a continuation of Ser. No. 598,730, Oct. 19, 1990, abandoned.

[30] Foreign Application Priority Data

Apr. 14, 1988 [GB] United Kingdom ............... 8808810

[51] Int. Cl.$^5$ ............ A61K 37/54; C08B 37/10; C12N 9/26; C12N 9/64
[52] U.S. Cl. ............... 424/94.62; 536/21; 435/201; 435/226
[58] Field of Search ............... 435/201, 226; 424/94.62, 94.63; 536/21

[56] References Cited

U.S. PATENT DOCUMENTS

| | | | |
|---|---|---|---|
| 2,976,212 | 3/1961 | Friedrich et al. | 424/94.62 |
| 4,390,630 | 6/1983 | Sawyer et al. | 435/226 |
| 4,410,531 | 10/1983 | Pope et al. | 424/94 |
| 4,568,543 | 2/1986 | Borrelli et al. | 424/94 |
| 4,801,452 | 1/1989 | Hunter et al. | 424/94.63 |
| 4,820,516 | 4/1989 | Sawyer et al. | 424/94.62 |

Primary Examiner—Douglas W. Robinson
Assistant Examiner—Susan M. Weber
Attorney, Agent, or Firm—Darby & Darby

[57] ABSTRACT

A method of treating thrombosis with a pharmaceutical formulation comprising an endo-beta-glucuronidase, preferably leech-derived, heparin and a pharmacologically acceptable diluent, carrier or excipient which does not prevent the interaction between the heparin and the endo-beta-glucuronidase is disclosed. The formulation, which is disclosed, can also comprise a clot-lytic agent such as tissue plasminogen activator. Endo-beta-glucuronidase, unlike other hyaluronidases, has been found not to be inhibited by heparin.

11 Claims, 5 Drawing Sheets

PHARMACEUTICAL FORMULATION CONTAINING HEPARIN AND ENDO-BETA-GLUCURONIDASE, USEFUL FOR THE TREATMENT OF THROMBOSIS

This is a continuation of application Ser. No. 07/840,617, filed Feb. 20, 1992, now abandoned, which is a continuation of application Ser. No. 07/598,730, filed Oct. 19, 1990, now abandoned.

The present invention is concerned with formulations containing heparin, and the use of hyaluronidases.

Heparin and its derivatives have been extensively used as anticoagulants for many years, both in pharmacologically active formulations and in formulations used in the treatment of apparatus, prostheses and transplants which come into contact with blood. The use of heparin as an anticoagulant is reviewed by, for example, Crawford, G. P. M. and Douglas, A. S. 1977 in Recent Advances in Blood Coagulation Ed. Poller, L. published by Churchill Livingstone.

Enzymes which cleave hyaluronic acid, or salts or derivatives thereof, are known as hyaluronidases. Hyaluronidases have previously been proposed for use in many formulations containing pharmacologically active ingredients, because of their ability to modify the permeability of tissue in vivo and therefore to act as "spreading" agents, resulting in enhanced delivery or penetration of the pharmacologically active material.

Byaluronidases have also been proposed for use in the reduction of myocardial ischaemia (the latter term meaning the irreversible damage of heart cells, as well as necrosis, which occurs consequent on the reduction of flow of blood through the cardiac muscle). However, if hyaluronidases were to be used for this purpose, they would almost certainly come into contact with heparin, which is used ubiquitously in cardiovascular surgery. In this case, the effectiveness of the therapy would be negated because certain hyaluronidases, in particular mammalian testicular hyaluronidase (abbreviated to MTH hereafter), are inhibited by very low levels of heparin.

Formulations containing both hyaluronidase and heparin have previously been proposed; for example, French Patent Specification 2101393 proposes a topical composition, for the treatment of psoriasis and other similar dermatological complaints (or for the treatment of varicose veins, tumours, local burns, haemorrhoids or the after-effects of phlebitis), which comprises a surface enzyme (such as a hyaluronidase), an anti-coagulant (such as heparin, dicoumarin or hirudin), and also a peripheral blood dilating agent (such as acetylcholine chloride or nicotinamide). Such formulations are described as ointments, creams, jellies, aerosols or foams. The type of hyaluronidase is not specified.

As we have described in our prior U.S. application Ser. No. 829,785 filed Feb. 14, 1986, now U.S. Pat. No. 4,820,516 issued Apr. 11, 1989, there are two basic types of hyaluronidase, which are those which are relatively non-specific and cleave hyaluronic acid, chondroitin and related polysaccharides, and those which specifically cleave hyaluronic acid only. The former are much more widely distributed in nature, being found in mammalian testes, liver and spleen and in certain microorganisms, while the latter are derived from certain other micro-organisms (such as streptomyces bacteria) and from leeches such as *Hirudo medicinalis* or leeches of the sub-family Hirudinariinae. These latter type cleave hyaluronic acid at a specific site and are termed endo-beta-glucoronidases.

Despite the previously proposed use of heparin in combination with a hyaluronidase, it has been demonstrated that certain hyaluronidases,(in particular, mammalian testicular hyaluronidase) are inhibited competitively by heparin (see Mathews & Dorfman, Physiological Review, 35, pp 381 to 402).

A prerequisite for use as a drug delivery vehicle is that the hyaluronidase enzyme should not be neutralised or inhibited by contact with blood or plasma. Surprisingly, we have now found that endo beta glucuronidases are unlike other hyaluronidases because they are not inhibited by heparin anticoagulant; thus according to the invention heparin and an endo-beta-glucuronidase can be coadministered to a patient without impairment of activity of the endo-beta-glucuronidase.

According to the present invention, therefore, there is provided a pharmaceutical formulation comprising heparin in combination with an endo-beta-glucuronidase. The formulation according to the invention further comprises a pharmacologically acceptable diluent, carrier or excipient therefor.

The formulation according to the invention may be in various forms. For example, it may be in a topically applicable form such as a cream, gel, ointment or aerosol; in this case it may be applied to, for example, an open wound or the like where it is desired to prevent coagulation of the blood. Alternatively, the formulation according to the invention may be a slow-release formulation such as a suppository or depot, or (preferably) an intravenous formulation. When referring to intravenous formulations, we mean formulations which can be injected as single or repeated unit doses by means of a hypodermic syringe or the like, or formulations which can be administered into the bloodstream continuously for a prolonged period, by means of a drip or the like. Such injectable intravenous unit doses are preferably provided in sealed sterile ampoules, in which the formulations according to the invention are present in liquid, frozen or lyophilised form.

In the latter case, the carrier is typically a buffered aqueous saline medium (typically buffered to a pH in the range 3 to 5.5), In which the aqueous carrier is sterile distilled (or otherwise highly purified) water (e.g. of purity at least 99.9% by weight). When the formulation according to the invention is intended for injection as a single or repeated dose, each unit dose preferably contains 20 thousand to 50 thousand units of the endo-beta-glucuronidase, one unit being defined as one microgram of glucose equivalent liberated per hour from hyaluronic acid at optimum pB. Approximately 20 such units correspond to one International Unit (I.U.) as described in 'International standard for hyaluronidase'; J. H. Humphrey, Bull. WHO; 16, pp. 291–294, 1957.

When the formulation according to the invention is intended for administration as an intravenous drip, the concentration of the endo-beta-glucuronidase is substantially less than the concentration in a formulation to be administered in discrete unit doses (e.g. in bolus form). For example, the concentration of the endo-beta-glucuronidase in an intravenously administerable composition according to the invention may be 10 to 1000 I.U. per kilogram body weight administered over a 24 hour period.

The concentration of heparin in the formulation according to the invention is typically 500 to 4000 I.U. over a 24 hour period administered subcutaneously, intravenously or by infusion; the endo-beta-glucuronidase and heparin are preferably present in a ratio of one I.U. of endo-beta-glucuronidase per two to six I.U. heparin.

The endo-beta-glucuronidase used in the formulation according to the invention may be derived from leeches of the sub-family Hirudinariinae, as described in more detail in the above-mentioned European patent specification. Alternatively, the endo-beta-glucuronidase may be derived from other species of leech, such as *Hirudo medicinalis*, or from other suitable sources. Just as in the abovementioned European patent specification, genetically engineered or synthetic equivalents to the endo-beta-glucuronoidase are intended to be encompassed by the term "derived from" leeches.

Heparin is an anticoagulant by virtue of its action against thrombin and other pro-coagulation factors. On the other hand, anticoagulation may also be achieved by plasminogen activator-mediated lysis of fibrin and/or fibrinogen thereby preventing clot formation; examples of such clot lytic agents are tissue-type plasminogen activator and hementin (a fibrinolytic or fibrinogenolytic agent derived from *Haementeria ghilianii*, as described in U.S. Pat. No. 4,390,630).

The formulation according to the invention may contain one or more further pharmacologically active ingredients; in a particularly preferred embodiment, the formulation according to the invention contains in addition one or more clot-lytic agent, such as prourokinase, urokinase, hementin, streptokinase or tissue plasminogen activator (tPA), and/or a derivative thereof. The clot-lytic agent is typically present in an amount of 500 to 3000 I.U. per kilogtam of body weight.

The present invention has been described in terms of a pharmaceutical formulation containing both heparin and an endo-beta-glucuronidase; the invention further comprises a method of therapeutic treatment of thrombotic events (such as the treatment of myocardial infarctions) in which the heparin and endo-beta-glucuronidase are administered to a patient either simultaneously or successively, optionally together with a clot-lytic agent as described above. The clot-lytic agent may be administered together with heparin and/or together with the endo-beta-glucuronidase, or as a separate administration.

Seen from another aspect, the present invention comprises an endo-beta-glucuronidase for use in therapy of a heparin-treated patient, optionally together with hementin and/or with tissue plasminogen activator.

The present invention is illustrated with reference to the following Examples:

EXAMPLE 1

Leech hyaluronidase (68 IU/ml was preincubated for one hour at 25° C. in the presence of concentrations of heparin (0-2500 USP/1 ml) in 20 mM methanesulphonic acid (MES), 0.1M NaCl, pH 5.0 buffer and then added to hyaluronic acid (5 mg/ml) and the incubation continued for one hour at 37° C. The generation of reducing sugars was determined by terminating the reactions by the addition of 1:1 3,5-dinitrosalicylic acid reagent (100 ml: 5% w/v dinitrosalicylic acid in 2M NaOH plus 250 ml: 60% w/v sodium potassium tartrate in water, made up to 500 ml with water) and heating for 5 min in vigorously boiling water. After heating, assay tubes were rapidly cooled to ambient temperature and absorbances at 540 nm measured spectrophotometrically. Suitable blanks and no-enzyme controls were included in the assay. The results are expressed as a percentage of the absorbances obtained in control incubations containing no heparin. Concentrations of heparin up to 2500 USP/ml had no significant effect on leech hyaluronidase activity, as indicated in the accompanying FIG. 1.

Figure 2:
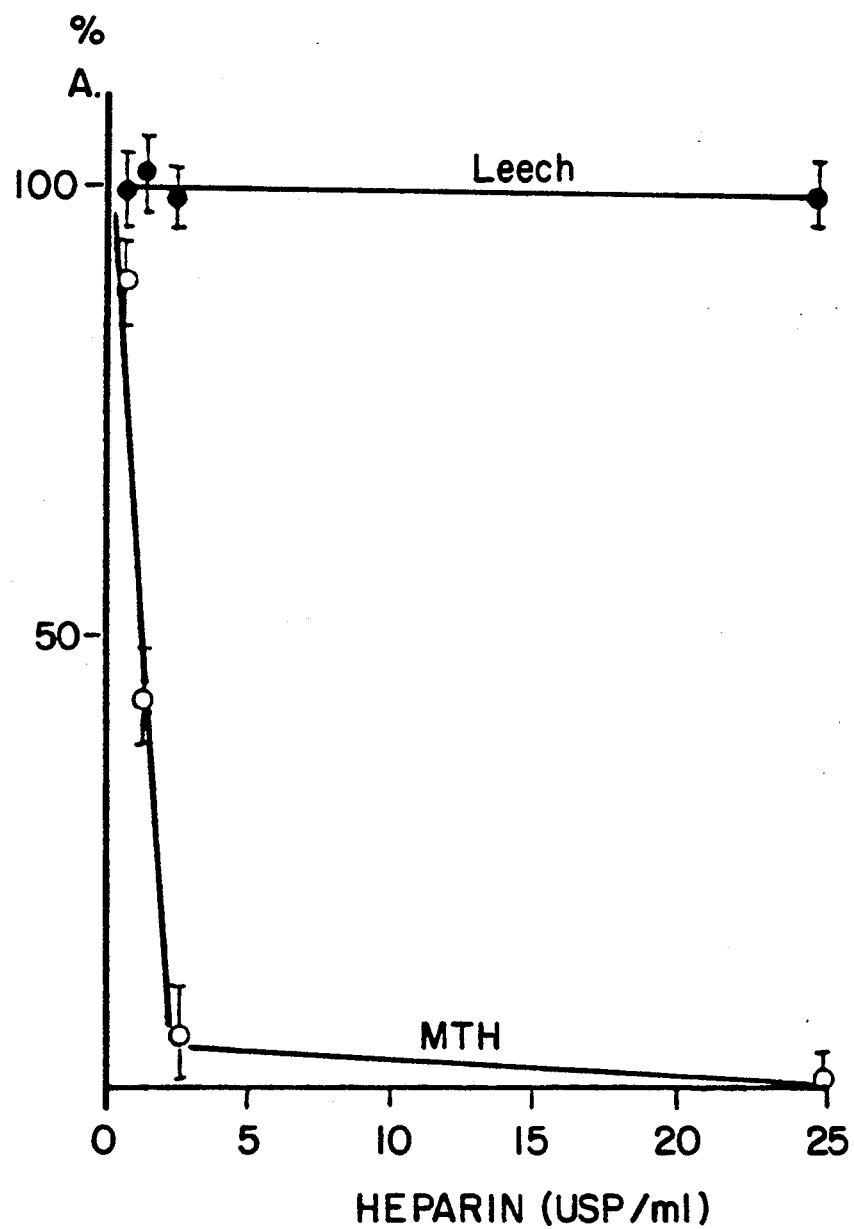

In striking contrast to leech hyaluronidase, mammalian testicular hyaluronidase (M-Tli) was completely inhibited by levels of heparin above 3 USP/ml (this being a plasma/serum level needed in vivo to induce an uncoagulated state). MTH (75 IU/ml) was preincubated for one hour at 25° C. with heparin (0 to 250 USP/ml) in 20 mM MES, 0.1M NaCl pH 5.0, buffer and then added (1:10 final dilution) to hyaluronate and incubated for a further one hour at 37° C. Activity was determined using using the reducing sugar assay (described above) and is expressed as a percentage of controls without heparin. The results obtained with leech hyaluronidese under identical conditions are shown in FIG. 2 of the accompanying drawings.

EXAMPLE 2

Heparin (0-150 USP/ml) was incubated for one hour at 370° C. either with or without leech hyaluronidase (50 IU/ml) and in 20 mM MES, 0.1M NaCl, pH 5.0 buffer; then whole blood was added to determine the effect on clottability. The results shown in the following Table 1, indicate that the leech hyaluronidase had not affected the ability of heparin to incoagulate blood.

TABLE 1

| Heparin (USP/ml) | Whole Blood Clotting Time (min) | |
|---|---|---|
| | Leech Enzyme | Leech Enzyme (50IU/ml) |
| 20 | NC | NC |
| 10 | NC | NC |
| 5 | NC | NC |
| 2.5 | 24.0 | 24.5 |
| 1.0 | 14.5. | 14.5 |
| 0 | 4.5 | — |

NC = no clot formation before 20 minutes at 37° C.

EXAMPLE 3

Leech hyaluronidase (100 IU/ml) was mixed 1:1 with Indian ink in 20 mM MES, 0.1M NaCl pH 5.0, buffer in the presence or absence of heparin (250 to 2500 USP/ml). Rats were injected subcutaneously with 50 microlitres of this mixture and spreading allowed to occur over a period of 1 to 3 hours. The rats were sacrificed and the skin removed for observation of the area of spreading.

The results, summarised in Table 2, show that in the presence of enzyme there was approximately a tenfold increase in the area of ink spreading cow-pared to controls and this was not significantly affected by relatively high doses of heparin.

TABLE 2

| | Heparin (USP/ml) | Area of spreading |
|---|---|---|
| Without enzyme | 0 / 250 / 2500 | Range 0.3 to 0.6 cm$^2$ |
| With enzyme | 0 / 250 / 2500 | Range 2.0 to 4.0 cm$^2$ |

EXAMPLE 4

Figure 3:
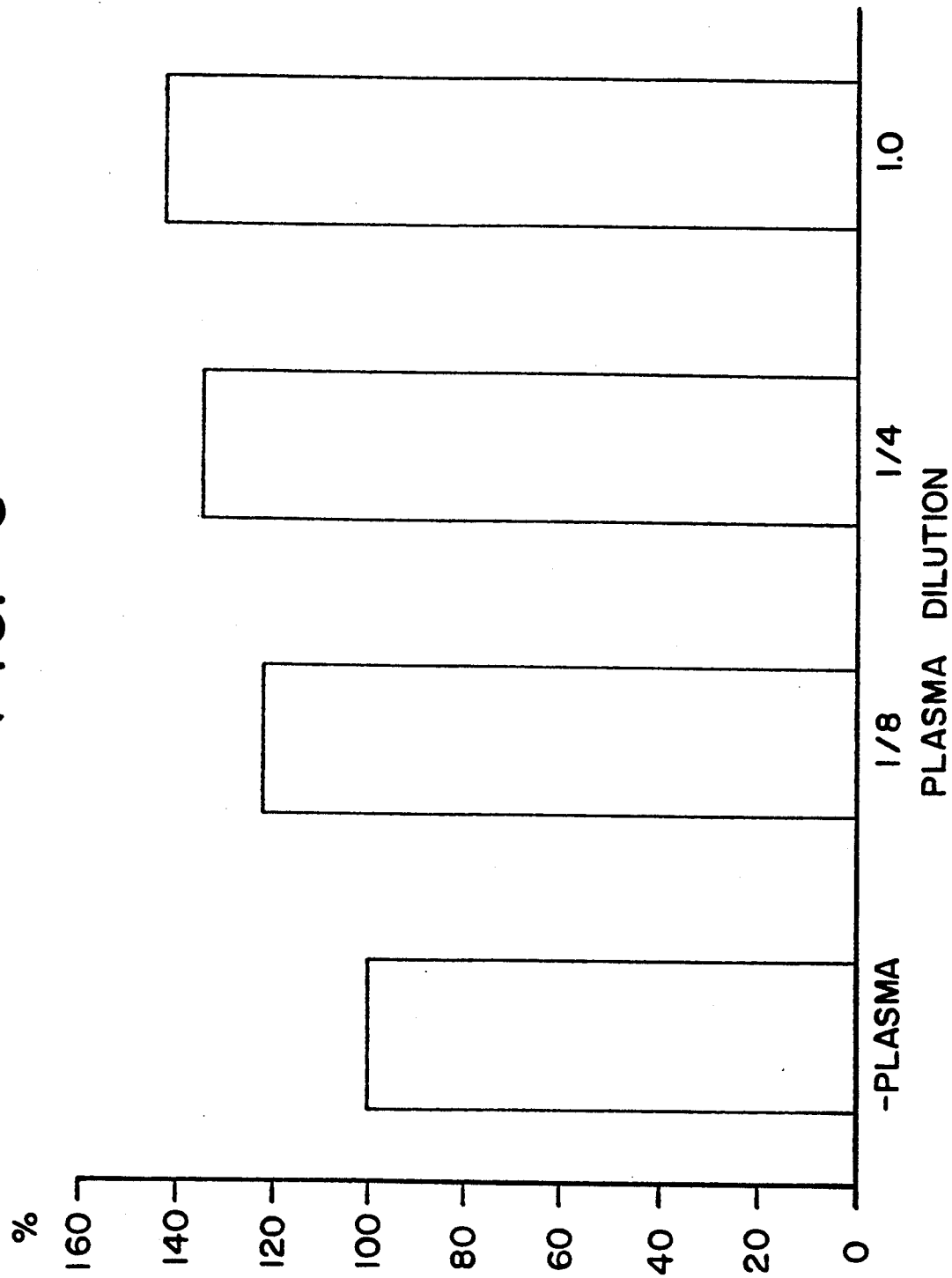

A) Leech hyaluronidase (200 IU/ml) was preincubated for one hour with dilutions of normal pooled citrated plasma in 20 mM MES, 0.1M NaCl pH 5.0 buffer and then added to hyaluronic acid (5 mg/ml) for a further one hour at 37° C. to determine reducing sugar activity (see Example 1 for method). The results, expressed as percent activity in the absence of plasma after subtraction of blanks are shown in FIG. 3 of the accompanying drawings. They show that the activity of the leech hyaluronidase is stimulated by the presence of plasma.

B) Leech hyaluronidase (200 IU/ml) was preincubated for one hour at 25° C. with and without plasma and heparinised plasma in 20 mM MES, 0.1M NaCl, pH 5.0 buffer. Plasma was obtained from a patient before and after heparinisation with 30,000 USP/24 h resulting in an increase in the clotting time of 40 seconds to 80 seconds. Incubations were continued by addition to hyaluronic acid (see section A, above) and reducing sugars determined as above (Example 1).

Figure 4:
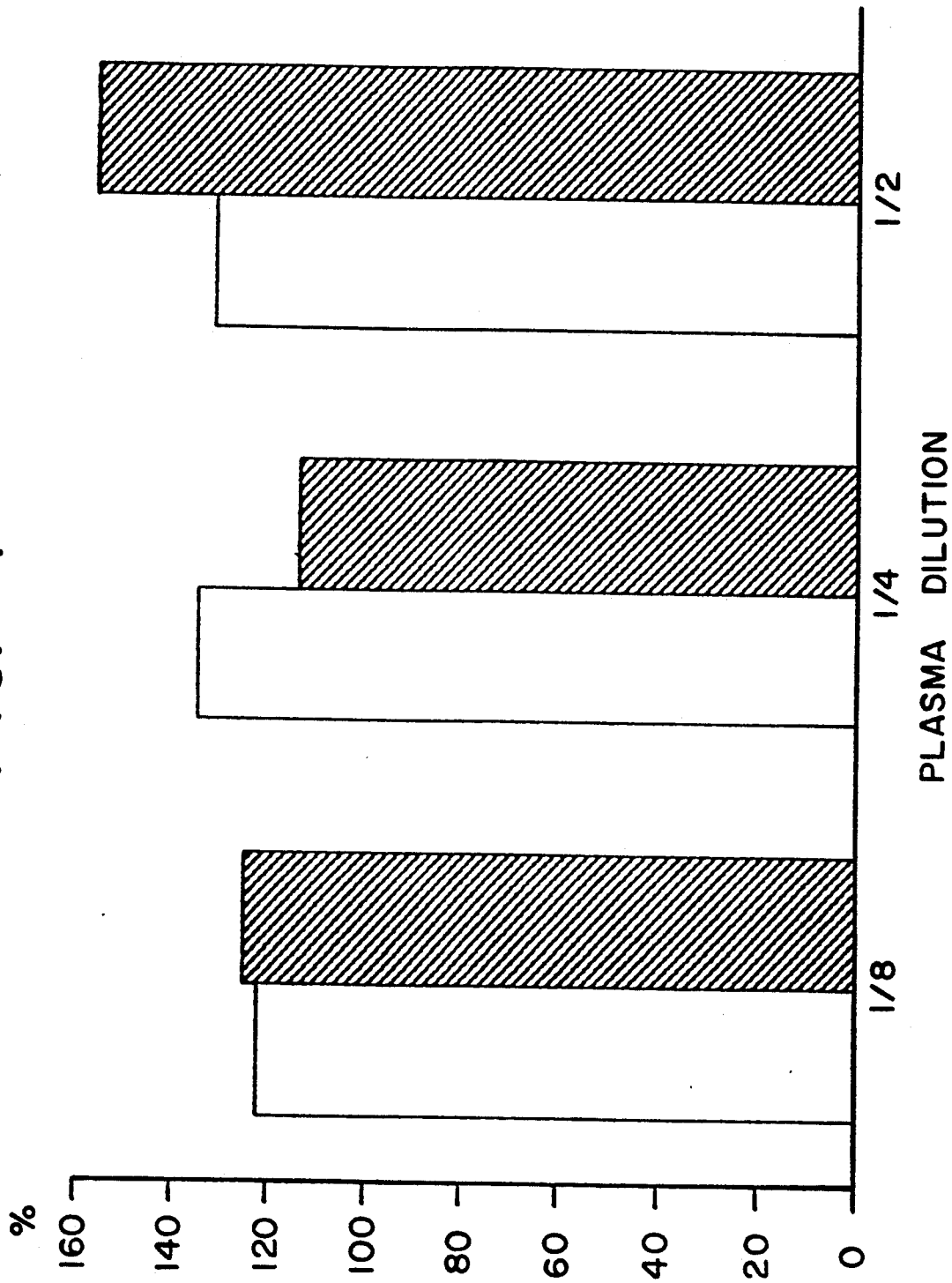

The results indicated no significant inhibition of leech hyaluronidase activity in heparinised plasma compared with non-heparinised plasma from the same patient, as shown in FIG. 4 (in which columns A represent runs without heparin and columns B represent runs with heparin).

EXAMPLE 5

A) Leech hyaluronidase (68 IU/ml) was mixed with and without heparin (200 USP/ml) and human tissue plasminogen activator (tPA) in a range of concentrations (0.5000 IU/ml) and with hyaluronic acid (5 mg/ml) and incubated for 1 h at 37° C. Reducing sugars were determined (Example 1) and results expressed as a percentage of controls containing no tPA.

Figure 5:
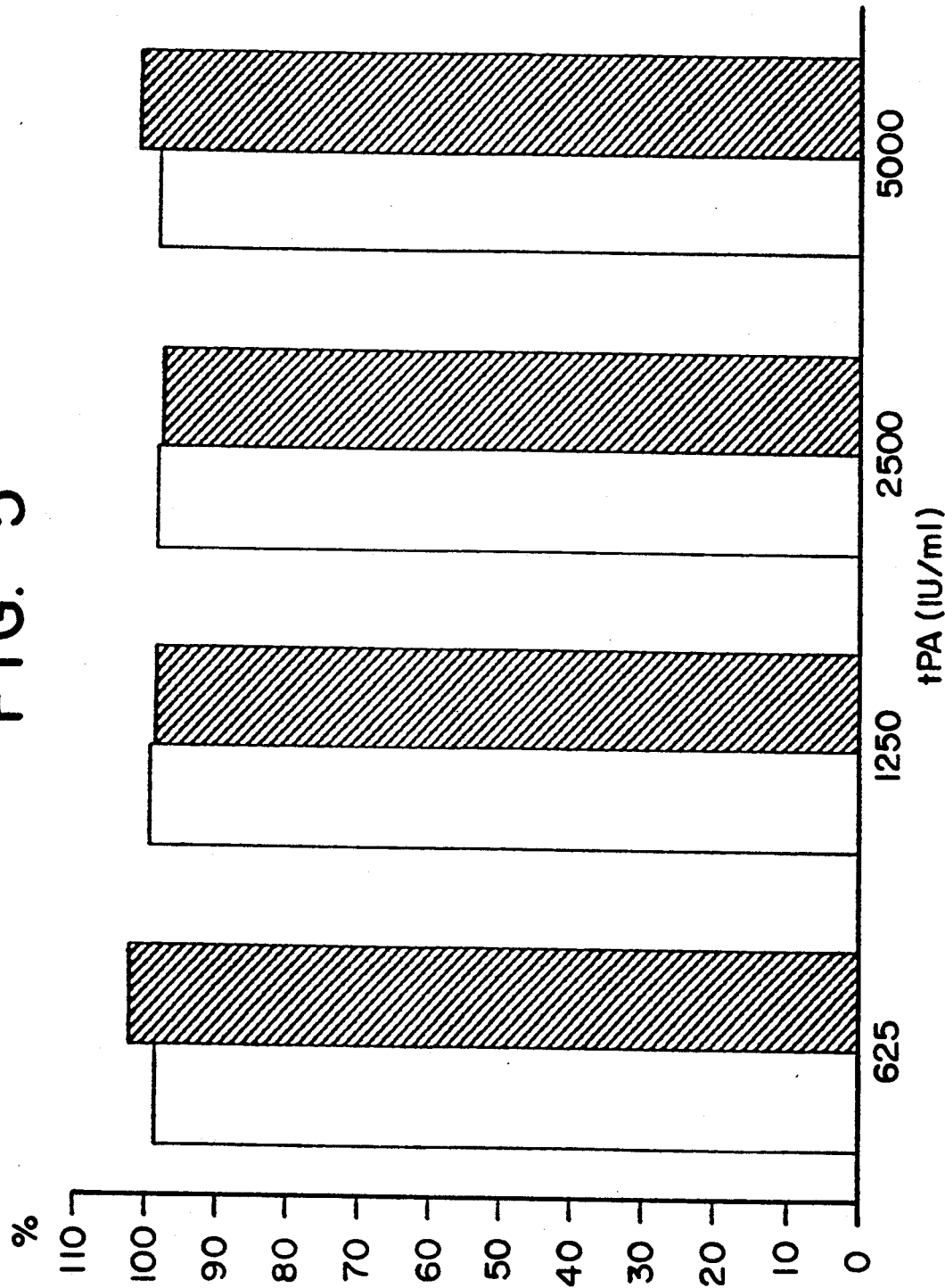

The results showed no effect of tPA on leech hyaluronidase activity either in the presence or absence of a relatively high dose of heparin, as shown in FIG. 5, in which columns A represent runs without heparin and columns B represent runs with heparin.

B) Leech hyaluronidase (75 IU/ml) was mixed with and without hementin (180 IU/ml) (where IU is defined as one microgram of fibrinogen incoagulated/min/37° C.) end incubated with heparin (1.5-1500 USP/ml) for one hour at 25° C. prior to addition to hyaluronic acid (2 mg/ml) and further incubation for one hour at 37° C. Reducing sugar levels were determined (see Example 1) and the results expressed as a percentage of controls containing no heparin. (Table 3).

TABLE 3

|  | Heparin (USP/ml) | % Control |
| --- | --- | --- |
| Without Hementin | 1.5 | 97.5 |
|  | 15 | 100 |
|  | 150 | 103 |
|  | 1500 | 103 |
| With Hementin | 1.5 | 103 |
|  | 15 | 93.8 |
|  | 150 | 100 |
|  | 1500 | 109 |

The results indicate substantially no effect of hementin on leech hyaluronidese activity in the presence or absence of heparin.

We claim:

1. A pharmaceutical formulation comprising an endo-beta-glucuronidase, heparin and a pharmacologically acceptable diluent, carrier or excipient, wherein said diluent, carrier or excipient does not prevent interaction between said heparin and said endo-beta-glucuronidase.

2. A formulation according to claim 1, wherein said endo-beta-glucuronidase is leech-derived.

3. A formulation according to claim 1 which further comprises at least one clot-lytic agent.

4. A formulation according to claim 1, which further comprises tissue plasminogen activator.

5. A formulation according to claim 1, which further comprises hementin.

6. A formulation according to claim 1, which is in a form suitable for intravenous administration.

7. An injectable unit dose, which comprises a sealed sterile ampoule containing a formulation according to claim 1.

8. A method for treating thrombosis by administering a therapeutically effective amount of a pharmaceutical formulation comprising an endo-beta-glucuronidase, heparin and a pharmacologically acceptable diluent, carrier or excipient, wherein said diluent, carrier or excipient does not prevent interaction between said heparin and said endo-beta-glucuronidase.

9. A method according to claim 8, wherein the formulation is administered intravenously.

10. A method according to claim 8, wherein said endo-beta-glucuronidase is leech derived.

11. A method according to claim 8, wherein said formulation further comprises at least one clot-lytic agent.

* * * * *